(12) United States Patent
Lin et al.

(10) Patent No.: US 10,940,174 B1
(45) Date of Patent: Mar. 9, 2021

(54) METHODS FOR SKIN WHITENING, ULTRAVIOLET RADIATION PROTECTION AND SUPPRESSION OF GLYCATION USING GREEN MANGO EXTRACTS AND COMPOUNDS OBTAINED THEREFROM

(71) Applicant: TCI CO., LTD., Taipei (TW)

(72) Inventors: Yung-Hsiang Lin, Taipei (TW); Chin-Hsiu Yu, Taipei (TW); Yu-Ming Chung, Taipei (TW)

(73) Assignee: TCI CO., LTD., Taipei (TW)

( * ) Notice: Subject to any disclaimer, the term of this patent is extended or adjusted under 35 U.S.C. 154(b) by 39 days.

(21) Appl. No.: 16/561,083

(22) Filed: Sep. 5, 2019

(51) Int. Cl.
| | |
|---|---|
| *A61K 36/00* | (2006.01) |
| *A61K 36/22* | (2006.01) |
| *A61P 17/16* | (2006.01) |
| *A61K 9/00* | (2006.01) |
| *A61K 31/7034* | (2006.01) |

(52) U.S. Cl.
CPC ............ *A61K 36/22* (2013.01); *A61K 9/0014* (2013.01); *A61K 31/7034* (2013.01); *A61P 17/16* (2018.01)

(58) Field of Classification Search
CPC ...................................... A61K 36/00
USPC .......................................... 424/725
See application file for complete search history.

(56) References Cited

FOREIGN PATENT DOCUMENTS

JP 2018203628 A * 12/2018

* cited by examiner

*Primary Examiner* — Michael V Meller
(74) *Attorney, Agent, or Firm* — Chieh-Mei Wang (57) ABSTRACT

Provided is a method for skin whitening, ultraviolet radiation protection, and anti-glycation by using a green mango extract. Also provided is a method for anti-glycation by using compounds of hydrolyzable tannins isolated from the green mango extract.

5 Claims, 10 Drawing Sheets

METHODS FOR SKIN WHITENING, ULTRAVIOLET RADIATION PROTECTION AND SUPPRESSION OF GLYCATION USING GREEN MANGO EXTRACTS AND COMPOUNDS OBTAINED THEREFROM

BACKGROUND OF THE INVENTION

1. Field of the Invention

The present invention relates to a method for skincare and healthcare by using a green mango extract and hydrolyzable tannins obtained therefrom. Particularly, the present invention relates to a method for skin whitening, ultraviolet radiation (UV) protection, and suppression of glycation by using the green mango extract; and a method for suppression of glycation by using the hydrolyzable tannins.

2. The Prior Art

The skin provides the first line protection for the body against ultraviolet radiation from the sun. The skin is made of the epidermis (including the outermost horny layer), dermis, and subcutaneous tissue, among which the epidermis is the outermost layer and is constantly renewed. Between the epidermis and the dermis are constantly dividing cells (such as fibroblasts, keratinocytes, and melanocytes), whose activities are very sensitive to ultraviolet light. The dermis contains collagen and elastin fibers, which impart elasticity and support to the skin. When exposed to high levels of ultraviolet radiation (mainly ultraviolet A), collagen and elastin fibers would be damaged, resulting in reduced skin elasticity, wrinkles, and the appearance of skin aging. In order to delay skin aging, it is important to decrease skin damage from UV irradiation.

Bright and translucent skin symbolizes youth and vitality. To display individual's vitality, modern people keep skin bright by make-up or skin care. Skin complexion depends mainly on the amount of melanin produced by melanocytes. Factors enhancing melanin production by melanocytes include congenital inheritance, endocrine disorders, lifestyle, sun exposure, and medication, which ultimately lead to dark skin or spots. Therefore, the development of methods for melanin production inhibition is crucial to skin whitening.

Another factor that causes skin aging is glycation, which is a non-enzymatic reaction between the aldehyde (ketone) group of reducing sugars and the amine group of amine-containing molecules such as proteins and nucleic acids. For individuals with long-term hyperglycemia, the proteins in the body are prone to glycation by glucose, leading to the formation of advanced glycation end products (AGEs). In addition to direct formation of AGEs in the body, AGEs also enter the body through dietary intake. Foods that have been overcooked or processed, such as the grilled or fried dish and bread, often contain higher amounts of AGEs. The proteins modified with AGEs would have impaired structures and physiological functions. Moreover, AGEs also increase the oxidative stress in cells and induce pro-inflammatory cytokine secretion, contributing to various metabolic diseases that accelerate aging, for example, atherosclerosis, neurodegenerative diseases, cataracts, and kidney failure. In terms of skin aging, glycation affects the packing of collagen fibers, and the glycated collagen fibers become stiff and brittle, resulting in increased wrinkles on the skin. Therefore, anti-glycation is another countermeasure to delay skin aging.

Currently, most of the ingredients for sun protection, skin brightening, or anti-glycation in commercially available skincare products are chemically synthesized. When used improperly, these ingredients may be harmful to skin health. Therefore, it is of necessity to develop a new type of skincare product with natural ingredients that are effective in skin whitening, UV protection, and anti-glycation.

SUMMARY OF THE INVENTION

Accordingly, in one aspect, the present invention provides a method for skin whitening, ultraviolet radiation (UV) protection, and anti-glycation, including the step of administering to a subject a composition including an effective amount of a green mango extract, wherein the green mango extract is obtained by extraction of a green mango with a solvent; and wherein the green mango is an unripe mango fruit with a length of 3 to 7 cm.

In one embodiment of the present invention, the weight ratio of the solvent to the green mango ranges from 20:1 to 1:1, and the extraction is performed at a temperature between 55° C. and 100° C.

In one embodiment of the present invention, the solvent is water, and the composition includes at least 0.25 mg/mL of the green mango extract.

In one embodiment of the present invention, the green mango extract inhibits melanin production, prevents and repairs ultraviolet A (UVA)-induced damage to skin fibroblasts, and suppresses glycation of collagen.

In another aspect, the present invention provides a method for anti-glycation, including the step of administering to a subject a composition including a pharmaceutically acceptable carrier and an effective amount of a compound represented by formula (I) or formula (II):

(I)

(II)

In one embodiment of the present invention, the compound of formula (I) or formula (II) is isolated from the aforementioned green mango extract. Not limited to preparation from green mango or other natural sources, the compounds may also be prepared by chemical synthesis.

In one embodiment of the present invention, the compound of formula (I) or formula (II) suppresses glycation of collagen.

In one embodiment of the present invention, the composition includes at least 100 μg/mL of the compound of formula (I) or formula (II).

The present invention discloses that the green mango extract has ultraviolet protection and skin-whitening effects on skin cells, and also inhibits protein glycation and avoids loss of normal structure and function of proteins due to glycation. Furthermore, the present invention also discloses the compounds of formula (I) and formula (II) that possess significant anti-glycation activities. Given that ultraviolet radiation, excessive melanin accumulation, and glycation all lead to the appearance of skin aging, especially glycation is one of the causes of body aging, and given that the green mango extract and compounds disclosed herein can be utilized in preparation of a composition for skin whitening, ultraviolet radiation protection, and anti-glycation, the present invention provides a new strategy to delay the aging of skin and even the aging of individuals. The composition may be in the form of powders, granules, solution, gel or paste and may be manufactured as a pharmaceutical composition, food, a drink, or a nutritional supplement that may be administered to a subject orally, topically or via other routes.

The present invention is further explained in the following examples, in reference to the accompanying drawings. It should be understood that the examples given below do not limit the scope of the invention, and that modifications can be made without departing from the scope of the appended claims.

BRIEF DESCRIPTION OF THE DRAWINGS

The present invention will be apparent to those skilled in the art from the following detailed description of the preferred embodiments, with reference to the attached drawings, in which.

DETAILED DESCRIPTION OF THE PREFERRED EMBODIMENT

Definition

Unless otherwise specified, "a", "the", and similar terms as used herein shall be interpreted to include the singular and plural.

Numerical quantities provided herein are approximated, experimental values that may vary within 20 percent, preferably within 10 percent, and most preferably within 5 percent. Thus, the terms "about" and "approximately" refer to within 20 percent, preferably within 10 percent, and most preferably within 5 percent of a given value or range.

The pharmaceutical composition described herein may be formulated, by techniques well known to those skilled in the art, into a dosage form suitable for topical, parenteral, or oral administration. The dosage form includes, but not limited to, injection (for example, sterile aqueous solution or dispersion), powders, tablets, troches, lozenges, pills, capsules, dispersible powders, granules, solutions, suspensions, emulsions, syrups, elixirs, slurries, and the like.

The pharmaceutical composition described herein may be administered via parenteral routes including, but not limited to, intraperitoneal injection, subcutaneous injection, intramuscular injection, and intravenous injection.

The pharmaceutical composition described herein may contain a pharmaceutically acceptable carrier that is widely used in the field of pharmaceutical manufacturing. The pharmaceutically acceptable carrier includes one or more agents selected from the group consisting of solvents, emulsifiers, suspending agents, decomposers, binding agents, excipients, stabilizing agents, chelating agents, diluents, gelling agents, preservatives, lubricants, absorption delaying agents, liposomes, and the like. The selection and amount for use of these agents are based on conventional techniques within the profession of those skilled in the art.

The aforementioned pharmaceutically acceptable carrier includes a solvent selected from the group consisting of water, normal saline, phosphate buffered saline (PBS), a sugar-containing solution, an aqueous solution containing alcohol, and combinations thereof.

Materials and Methods

Materials

Dulbecco's modified Eagle's medium (Gibco DMEM), Eagle's minimum essential medium (Gibco MEM), fetal bovine serum (Gibco FBS), penicillin/streptomycin (Gibco), phosphate buffered saline (Gibco PBS), sodium pyruvate, sodium bicarbonate, and non-essential amino acids were purchased from Thermo Fisher Scientific. 3-(4,5-dimethylthiazol-2-yl)-2,5-diphenyltetrazolium bromide (MTT) used in cell viability assay was purchased from AMERSCO. Dimethyl sulfoxide (DMSO) was purchased from Echo Chemical.

Solvents, including n-hexane, ethyl acetate, acetone, methanol, ethanol, acetonitrile, chloroform-$d_1$ (deuteration degree 99.5%), methanol-$d_6$ (deuteration degree 99.5%), heavy water (deuterium oxide, deuteration degree>99.8%), and dimethyl sulfoxide-$d_6$ (deuteration degree>99.9%) were purchased from Merck Taiwan.

Instruments for Chemical Analysis

Compounds are isolated using column chromatography and thin layer chromatography (TLC). Medium pressure liquid chromatography (MPLC) was performed on the CombiFlash® Rf+ (Teledyne ISCO) system; and the column medium was selected from Sephadex LH-20 (Amersham Biosciences), Diaion HP-20 (Mitsubishi Chemical), Merck Kieselgel 60 (40-63 µm, Art. 9385), and Merck LiChroprep® RP-18 (40-63 µm, Art. 0250). The high performance liquid chromatography (HPLC) system was equipped with Hitachi L-2310 series pump, Hitachi L-2420 UV-VIS detector (detection wavelength ranging from 200 nm to 380 nm), and D-2000 Elite software for data processing; and the column was selected from analytical columns Discovery® HS $C_{18}$ (250×4 6 mm, 5 µm; SUPELCO) and Mightysil RP-18 GP 250 (250×4.6 mm, 5 µm; Kanto Chemical), semi-preparative column Discovery® HS $C_{18}$ (250×10 0 mm, 5 µm; SUPELCO) and preparative column Discovery® HS $C_{18}$ (250×21.0 mm, 5 µm; SUPELCO). The chromatography system was equipped with UV lamp UVP UVGL-25 (wavelength 254 nm and 365 nm). The TLC aluminum plate was coated with the silicone gel 60 $F_{254}$ (0.25 mm; Merck) or RP-18 $F_{254S}$ (0.25 mm; Merck).

The chemical structure of compounds was determined by mass spectrometry (MS) and nuclear magnetic resonance spectrometry (NMR). Specifically, tandem mass spectrometer (MS/MS; Bruker amaZon SL system and Thermo Orbitrap Elite system) with two-dimensional ion trap, Fourier transform analyzer, and electrospray ionization (ESI) was employed; and one-dimensional and two-dimensional NMR spectra were obtained by Varian 400 FT-NMR spectrometer operating at 400 MHz, with tetramethylsilane (TMS) as an internal standard ($\delta$=0).

Cell Culture

Cells used in the following examples include mouse melanoma cells B16F10 (ATCC CRL-6475) and human skin fibroblasts CCD-966SK (ATCC CRL-1881), both of which were purchased from the American Type Culture Collection (ATCC). B16F10 cells were cultured at 37° C. under 5% carbon dioxide in DMEM supplemented with 10% FBS and 1% penicillin/streptomycin, hereinafter referred to as DMEM culture medium. CCD-966SK cells were cultured at 37° C. under 5% carbon dioxide in MEM supplemented with 10% FBS, 1 mM sodium pyruvate, 1.5 g/L sodium bicarbonate, 0.1 mM non-essential amino acids, and 1% penicillin/streptomycin, hereinafter referred to as MEM culture medium.

Melanin Production Assay

The melanin levels in B16F10 melanoma cells were determined according to procedures described below. Cells were harvested from the cell culture treated as indicated. The cells were washed with PBS and treated with trypsin for 3 minutes. The suspended cells were collected by centrifugation (400×g, 5 minutes), washed twice with PBS, and then resuspended in 200 µL of PBS. The cell suspension was frozen in liquid nitrogen for 10 minutes and then left at room temperature for about 30 minutes until completely thawed, followed by centrifugation (12,000 g, 3 minutes) to remove the supernatant. The remaining cell pellet was mixed thoroughly with 120 µL of 1 N sodium hydroxide aqueous solution, and heated at 60° C. for 1 hour to obtain a cell lysate containing dissolved melanin. 100 µL of the cell lysate was transferred to a 96-well plate, and the absorbance at 450 nm (OD450) was measured using an enzyme-linked immunosorbent assay (ELISA) reader (BioTek). The relative melanin level is calculated according to the following formula:

$$\text{Relative melanin level (\%)} = (OD450_{each\ group} / OD450_{mock\ control}) \times 100\%$$

MTT Assay

Cell viability was determined by MTT assay. Briefly, an MTT solution (4 mg/mL MTT in PBS) was added to cells in a 96-well plate at 15 µL/well for reaction at room temperature for 4 hours. After the solution was discarded, DMSO was added to the cells at 50 µL/well and the mixture was incubated with shaking for 10 minutes to dissolve the resulted formazan crystals. Finally, the absorbance at 570 nm (OD 570) was measured using an ELISA reader (BioTek). Cell viability is calculated according to the following formula:

$$\text{Cell viability} = (OD570_{each\ group} / OD570_{mock\ control}) \times 100\%$$

Statistical Analysis

Data are expressed as mean±standard deviation (SD). Statistical analysis was performed using the Excel software; the statistical significance of the differences between the data was determined by Student's t-test.

Example 1

Preparation of the Green Mango Extract

The mango (*Mangifera indica*) described herein refers to the mango cultivars of Taiwan origin, but is not limited thereto. In general, the growth and development of mango fruit is divided into four periods as follows: (1) the young fruit period, at which the fruit begins to grow slowly after the mango flower is thanked and the fruit looks green; (2) the rapid growing period, at which the fruit enlarges fast and the starch in the flesh gradually accumulates; (3) the maturation period, which starts when the endocarp of the fruit hardens; during this period, the fruit appearance does not change much but the weight of the fruit continues to increase, and certain physical and chemical changes are continuously taking place, for example, the fruit hardness decreases, the sugar content increases, the peel turns yellow, which cause the fruit to ripen completely and become edible; (4) the aging period, which starts when the fruit is completely ripe. The green mango or unripe mango fruit described herein refers to the mango fruit that has not entered the maturation period and the peel has not turned yellow.

For preparation of a green mango extract, an unripe mango fruit with a length of about 3 to 7 cm is ground using a homogenizer. Thereafter, the green mango homogenate is extracted by using water, an alcohol, or an alcohol-water mixture as the solvent, to which 0.1% to 5% of a mix of organic acid (such as acetic acid and citric acid) and hydrochloric acid may be added. The weight ratio of the solvent to the green mango homogenate ranges from 20:1 to 1:1. The extraction temperature is between 55° C. and 100° C., preferably between 55° C. and 85° C. In the following Examples 2-5, all the green mango extracts were obtained by extraction of the green mango with an aqueous solution containing 0.1% to 0.5% of acetic acid, citric acid and hydrochloric acid, and the time for extraction is from 0.5 to 3 hours.

After the abovementioned extraction, the green mango extract is cooled to room temperature. The extract may be centrifuged at 3,000 to 5,000 rpm for 5 to 10 minutes at room temperature to obtain a supernatant, and the supernatant may be filtered through a 400 mesh filter to remove residual solids. Furthermore, the filtered green mango extract may be concentrated under reduced pressure (less than 1 atm) at 45° C. to 70° C. to obtain a concentrated product. In order to obtain a solid form of green mango extract, the solvent is removed from the concentrated green mango extract by a drying method such as freeze drying, spray drying, or the like, thereby obtaining the powder of green mango extract.

Example 2

Inhibition of Melanin Production by the Green Mango Extract

In order to examine the effect of the green mango extract on melanin production, the melanoma cells B16F10 was assayed for melanin production after treatment with the green mango extract described in Example 1. Briefly, B16F10 cells were seeded at $1.5 \times 10^5$/well in a 6-well plate, where each well contained 3 mL DMEM culture medium. After cell culture at 37° C. for 24 hours, the culture medium was removed, and the cells in each well were treated with 3 mL of DMEM culture medium containing 0.25 mg/mL of the green mango extract (experimental group) or 0.25 mg/mL of kojic acid (as positive control). Cells treated with 3 mL DMEM culture medium alone were used as a mock control. After cultured at 37° C. for 48 hours, the cells from the three groups were collected for determination of the melanin levels (experiments in triplicate).

Figure 1:
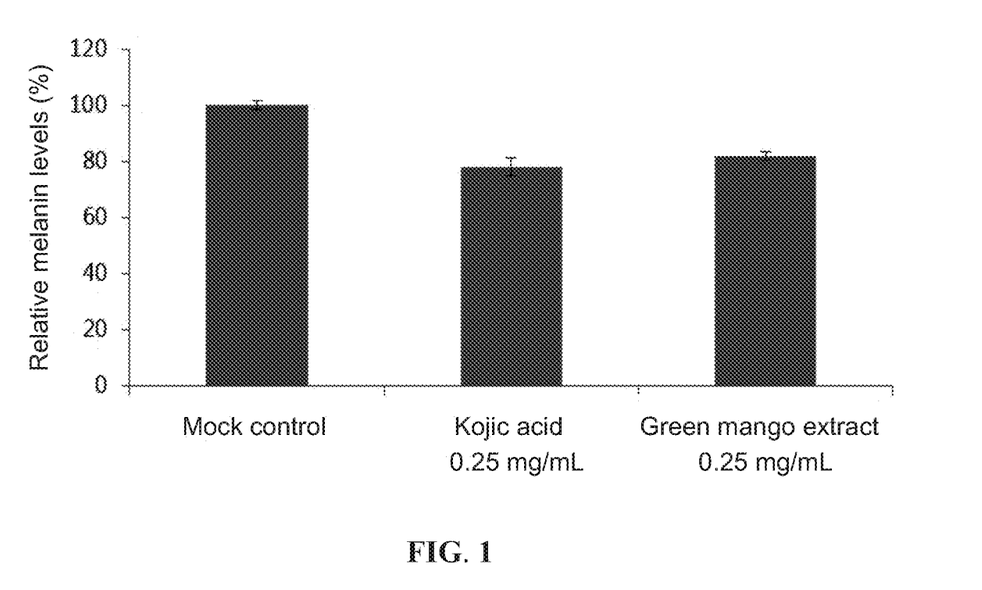
FIG. 1 shows the relative melanin levels in melanoma cells B16F10 treated with kojic acid or a green mango extract according to one embodiment of the present invention.

FIG. 1 shows the relative melanin levels in the melanoma cells from the three groups. According to this figure, administration of the green mango extract significantly reduced the melanin level by about 18% compared to the mock control, and this inhibitory effect on melanin production was comparable to that of the same concentration of kojic acid, a compound well-known as a skin whitening agent. The result indicates that the green mango fruit extract has an inhibitory effect on melanin production that is equivalent to that of the conventional skin whitening compound.

Example 3

Prevention and Reduction of UVA-Induced Death of Skin Fibroblasts by the Green Mango Extract In order to examine the protective effect of the green mango extract on the skin against ultraviolet radiation, MTT assay was employed to assess the viability of human skin fibroblasts CCD-966SK either pretreated with the green mango extract described in Example 1 and then irradiated with UVA (assessment for prevention of UVA-induced damage), or first irradiated with UVA and then treated with the green mango extract described in Example 1 (assessment for repair of UVA-induced damage).

3.1 Assessment for Prevention of UVA-Induced Damage

CCD-966SK cells were seeded at $5 \times 10^3$ cells/well in a 96-well plate, where each well contained 200 μL of MEM culture medium. After cell culture at 37° C. for 24 hours, the culture medium was removed, and the cells in each well were treated with 200 μL of MEM culture medium alone or the medium containing 0.5 mg/mL of the green mango extract. After cultured at 37° C. for another 24 hours, the cells were treated in the following manner: (a) the cells without pretreatment with the green mango extract were cultured for 1 hours without UV irradiation (mock control); (b) the cells without pretreatment with the green mango extract were irradiated with 15 $J/cm^2$ UVA (half lethal dose for the cells) in a UV chamber (Vilber) for 1 hour (UVA group); or (c) the cells pretreated with the green mango extract were irradiated with 15 $J/cm^2$ UVA for 1 hour (green mango extract+UVA group). Thereafter, the cells from each group were subjected to MTT assay to determine cell viability.

Figure 2:
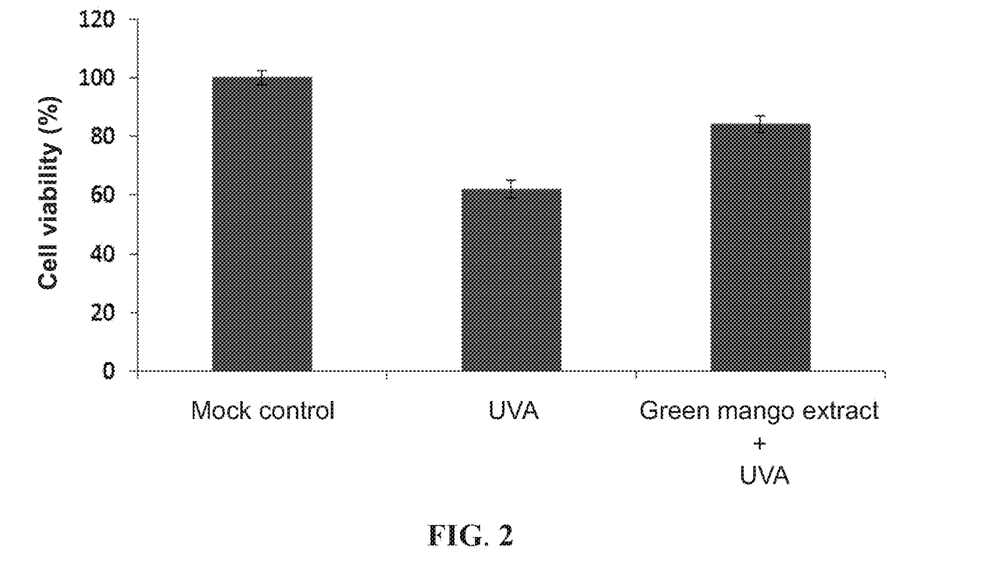
FIG. 2 shows the viability of skin fibroblasts pretreated with a green mango extract according to one embodiment of the present invention and then irradiated with ultraviolet A light.

FIG. 2 shows the viability of skin fibroblasts after different treatments. According to FIG. 2, the cell viability for the UVA group was about 61.8% compared with the mock control, indicating that UVA radiation kills a large number of skin fibroblasts. Compared to the UVA group, pretreatment with the green mango extract increased the viability of cells under UV irradiation to about 84.1%. The result indicates that administration of the green mango extract can prevent UV-induced damage or death of skin cells.

3.2 Assessment for Repair of UVA-Induced Damage

CCD-966SK cells were seeded at $5 \times 10^3$ cells/well in a 96-well plate, where each well contained 200 μL of MEM culture medium. After cell culture at 37° C. for 24 hours, the cells in each well were treated in the following manner and the culture medium was replenished: (a) 200 μL MEM culture medium alone was applied after the cells were cultured for 1 hour without UVA irradiation (mock control); (b) 200 μL MEM culture medium alone was applied after the cells were irradiated with 15 $J/cm^2$ UVA for 1 hour (UVA group); or (c) 200 μL MEM culture medium containing 0.5 mg/mL of the green mango extract was applied after the cells were irradiated with 15 $J/cm^2$ UVA for 1 hour (UVA+ green mango extract group). After cultured at 37° C. for 24 hours, the cells from each group were subjected to MTT assay to determine cell viability.

Figure 3:
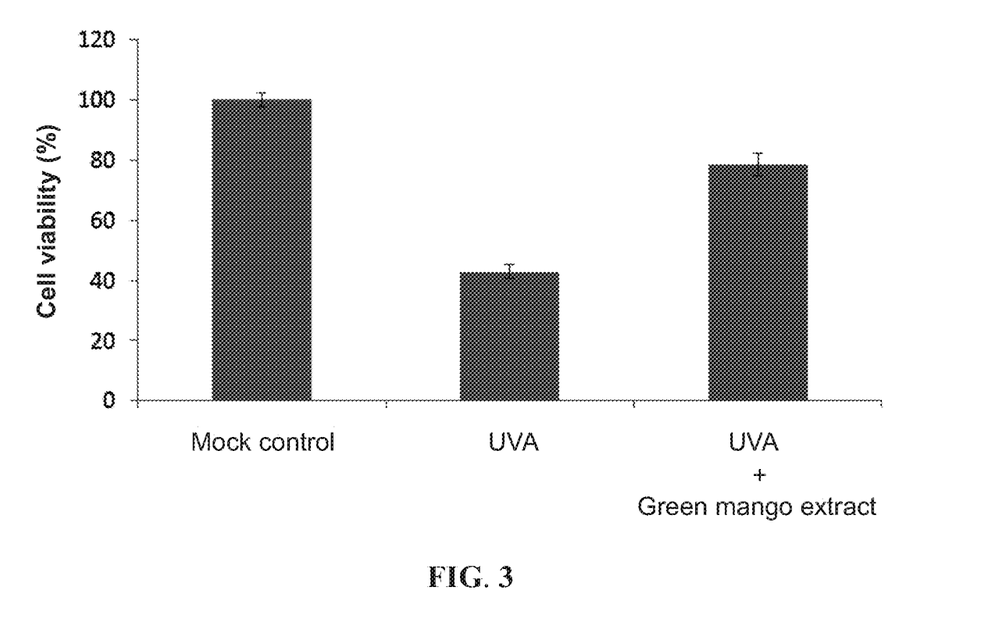
FIG. 3 shows the viability of skin fibroblasts irradiated with ultraviolet A light and then treated with a green mango extract according to one embodiment of the present invention.

FIG. 3 shows the viability of skin fibroblasts after different treatments. According to FIG. 3, the cell viability for the UVA group was about 42.9% compared with the mock control, whereas the viability of the UV-irradiated cells treated with the green mango extract increased to about 78.4%. The result indicates that administration of the green mango extract can reduce or repair the UV-induced damage to skin cells.

Example 4

Suppression of Glycation by the Green Mango Extract

In order to evaluate the anti-glycation activity of the green mango extract, an anti-glycation assay was performed to determine the inhibitory effect of the green mango extract described in Example 1 on glycation of porcine collagen. Briefly, a 60 mg/mL collagen solution (containing 0.06% sodium azide) and a 1.5 M fructose solution were first prepared using a 200 mM phosphate buffer (pH 7.4). For collagen to undergo glycation, a mixture of 0.2 mL of the collagen solution and 0.2 mL of the fructose solution was mixed thoroughly with 0.2 mL of the green mango extract sample at 140, 70, 14, 1.4, or 0.14 mg/mL (diluted with deionized water), or mixed with deionized water (as a control). The reaction mixtures were incubated at 50° C. for 24 hours. Thereafter, aminoguanidine (AG, purchased from Sigma) was added to terminate the glycation reaction. The fluorescence intensity (excitation wavelength at 360 nm, detection wavelength at 460 nm) of each of the reaction mixtures (0.1 mL) at 0 hour and 24 hours was measured using a fluorescence plate reader (FLx 800, BioTek), and the rate of AGEs formation due to collagen glycation was calculated according to the following formula:

AGEs formation rate=[(fluorescence intensity at 24 hours−fluorescence intensity at 0 hour)$_{sample}$/ (fluorescence intensity at 24 hours−fluorescence intensity at 0 hour)$_{control}$]×100%

Figure 4:
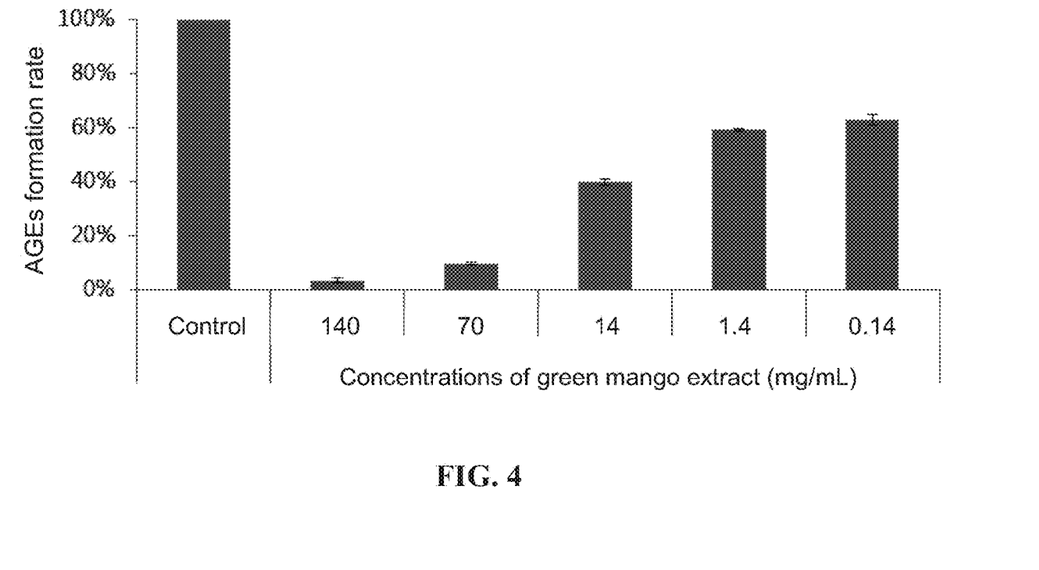
FIG. 4 shows the effect of a green mango extract according to one embodiment of the present invention on AGEs formation due to collagen glycation.

FIG. 4 shows the effect of the green mango extract on the AGEs formation due to collagen glycation. According to this figure, treatment with 140, 70, 14, 1.4, or 0.14 mg/mL of the green mango extract significantly reduced AGEs formation to about 3.6%, 9.6%, 39.7%, and 59.2%, and 62.9%, respectively, compared to the control, indicating that the green mango extract can inhibit protein glycation in the body, thereby delaying the aging of individuals.

Example 5

Preparation and Identification of the Compounds of Formula (I) and Formula (II)

In order to obtain the active ingredients in the green mango extract that suppresses glycation, firstly, 1 L of the green mango extract was prepared according to the method described in Example 1, and the extract was further extracted three times by liquid-liquid partitioning using ethyl acetate and water at equal proportion. The resulting ethyl acetate fractions were pooled and then concentrated to dryness under reduced pressure to yield about 4.7 g of an ethyl acetate extract.

Following bioassay-guided fractionation, the ethyl acetate extract (about 4.7 g) was subjected to Diaion HP-20 column chromatography using mixed water and methanol with decreasing polarity gradient as the eluent, and three fractions (respectively denoted as F1 to F3) were obtained. Thereafter, each of the F2 and F3 fractions was subjected to Sephadex LH-20 column chromatography using a methanol eluent, and each of the eluted solutions was then separated by TLC to obtain three fractions (respectively denoted as F2-1 to F2-3 and F3-1 to F3-3). The F3-2 fraction was further subjected to HPLC (employing a C18 column) using a mixture of water and methanol in a volume ratio of 1:1 as the mobile phase, and finally compound 1 was isolated in an amount of about 13.0 mg. Also, the F2-1 fraction was further subjected to HPLC (employing a C18 column) using a mixture of water and methanol in a volume ratio of 2:1 as the mobile phase, and finally compound 2 was isolated in an amount of about 23.0 mg.

Figure 5:
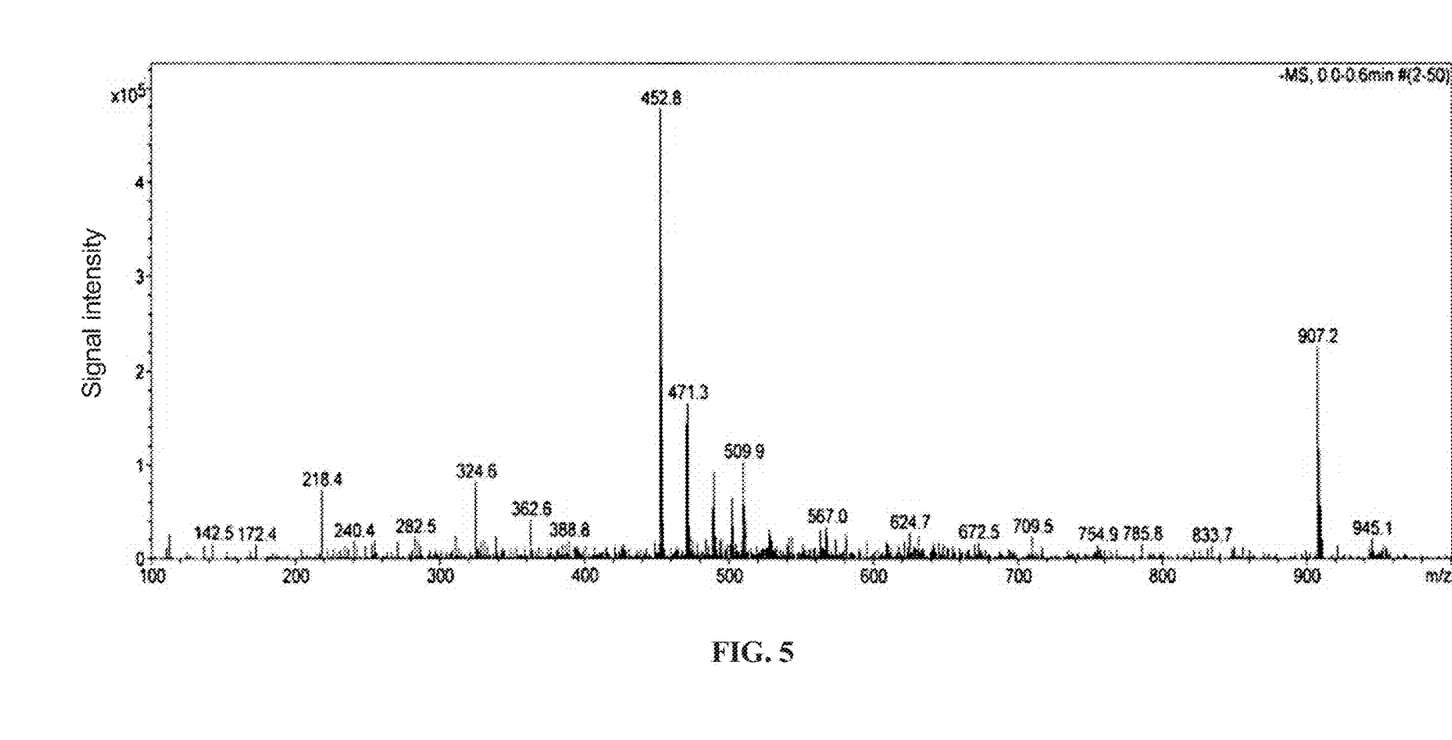
FIG. 5 shows the mass spectrum for compound 1.
Figure 6A:
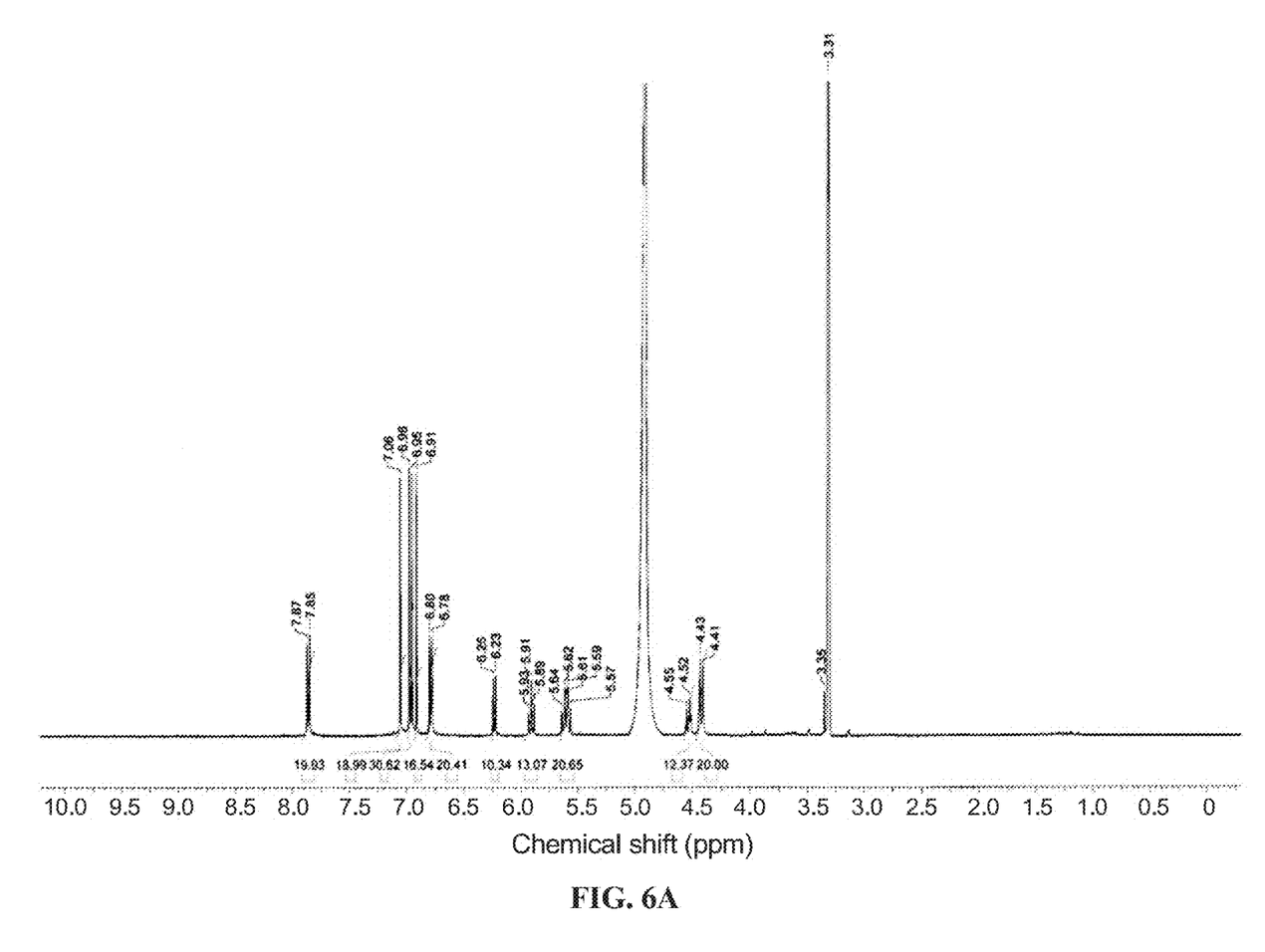
FIG. 6A shows the hydrogen nuclear magnetic resonance ($^1$H-NMR) spectrum for compound 1.
Figure 6B:
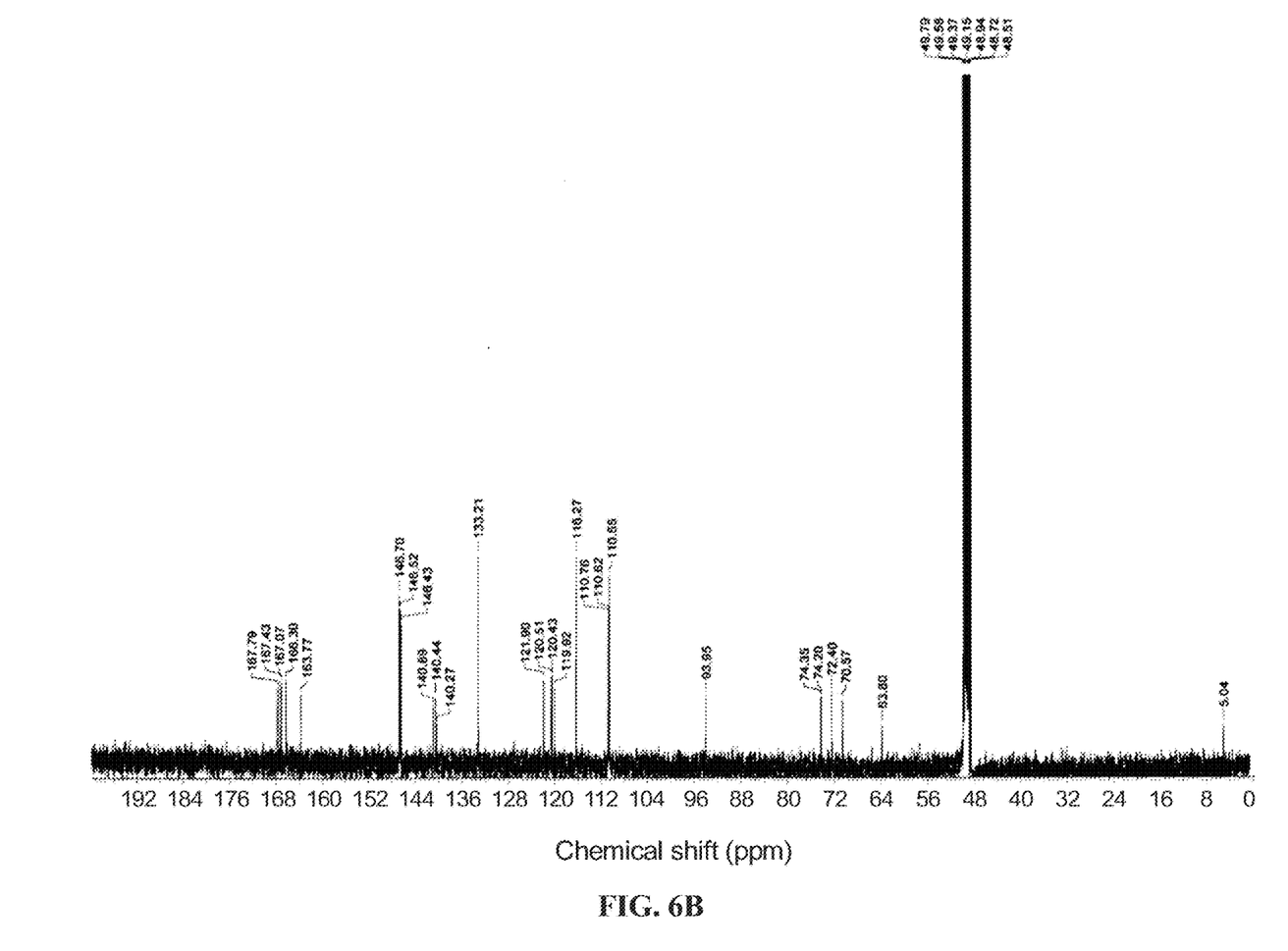
FIG. 6B shows the carbon nuclear magnetic resonance ($^{13}$C-NMR) spectrum for compound 1.

The chemical structures of compound 1 and compound 2 were determined by mass spectrometry and nuclear magnetic resonance spectroscopy (NMR). Compound 1 is a light brown oil. From the mass spectrum shown in FIG. 5, a pseudo-molecular ion peak at m/z 907 [M-H]− is observed, so that compound 1 is estimated to have a molecular weight of 908 Da. According to the $^1$H-NMR spectrum shown in FIG. 6A, compound 1 has a main structure composed of a sugar group and five aromatic rings. According to the $^{13}$C-NMR spectrum shown in FIG. 6B, compound 1 has a total of 41 carbon absorption signals, which are 5 carbonyl absorption signals, 5 benzene ring absorption signals, and one set of glycosyl absorption signals. Furthermore, according to the two-dimensional NMR spectra (COSY, HSQC, and HMBC) shown in FIGS. 6C to 6E, the connection between the single sugar group and the five aromatic rings and the position of the substituents in the compound 1 can be inferred.

Figure 6C:
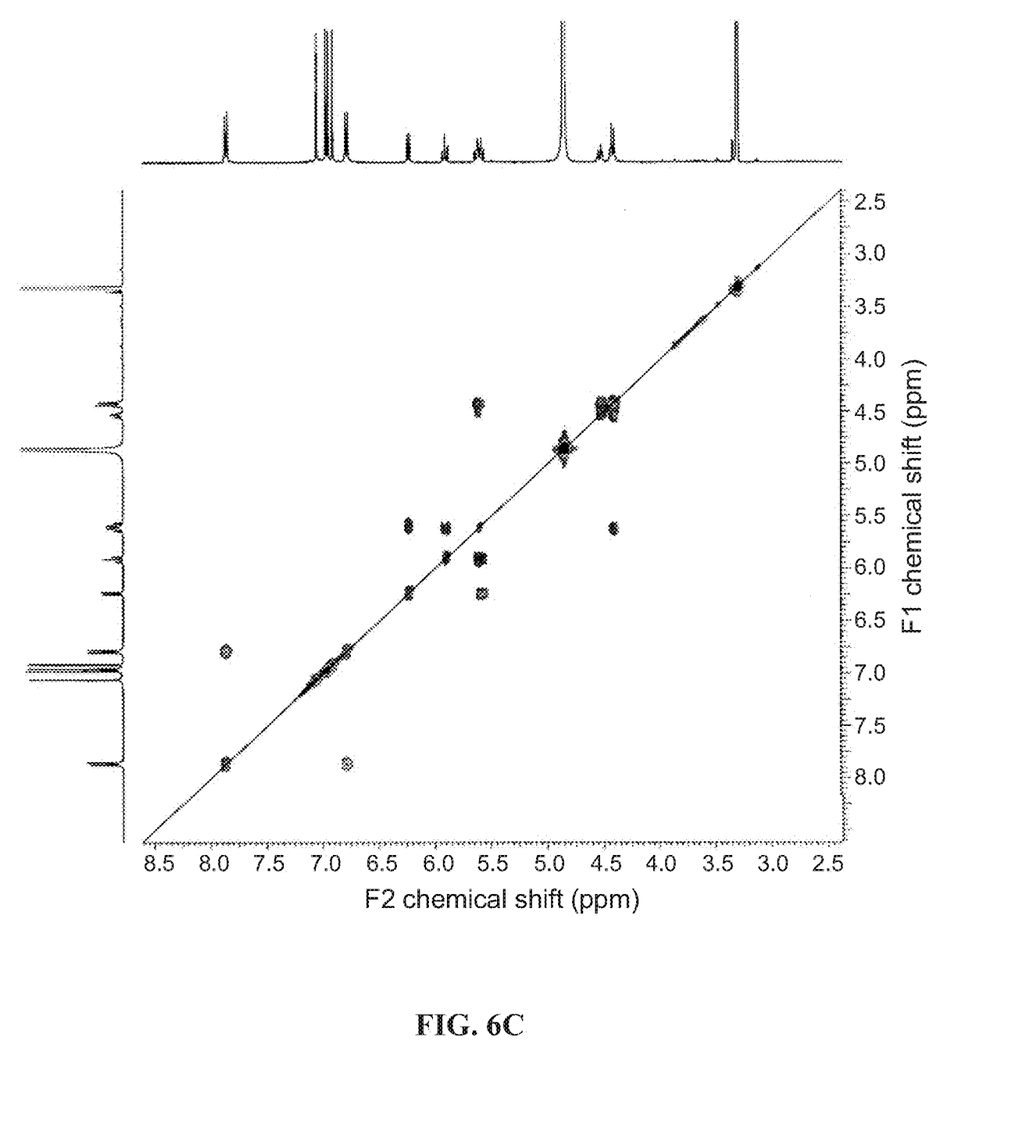
FIG. 6C shows the correlation spectroscopy (COSY) spectrum for compound 1.
Figure 6D:
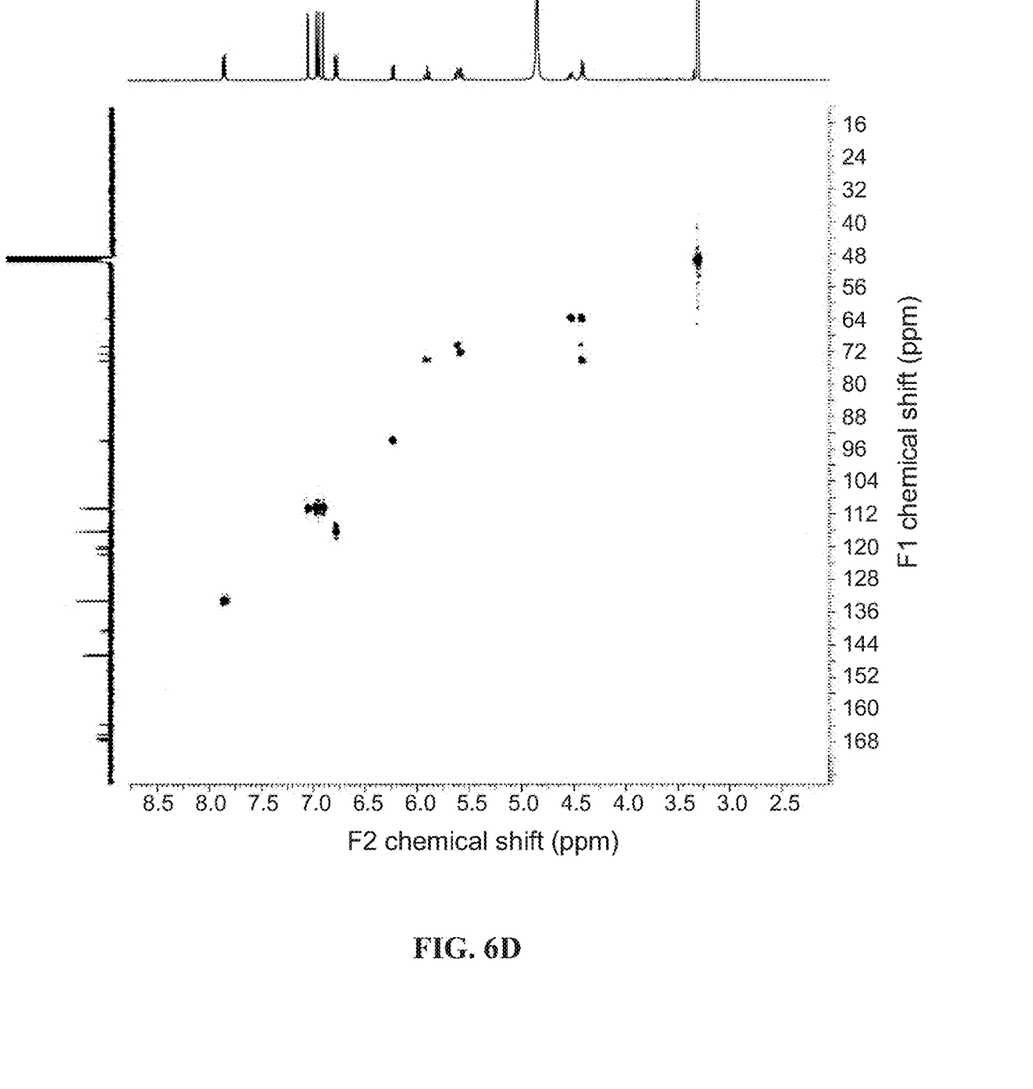
FIG. 6D shows the heteronuclear single quantum correlation (HSQC) spectrum for compound 1.
Figure 6E:
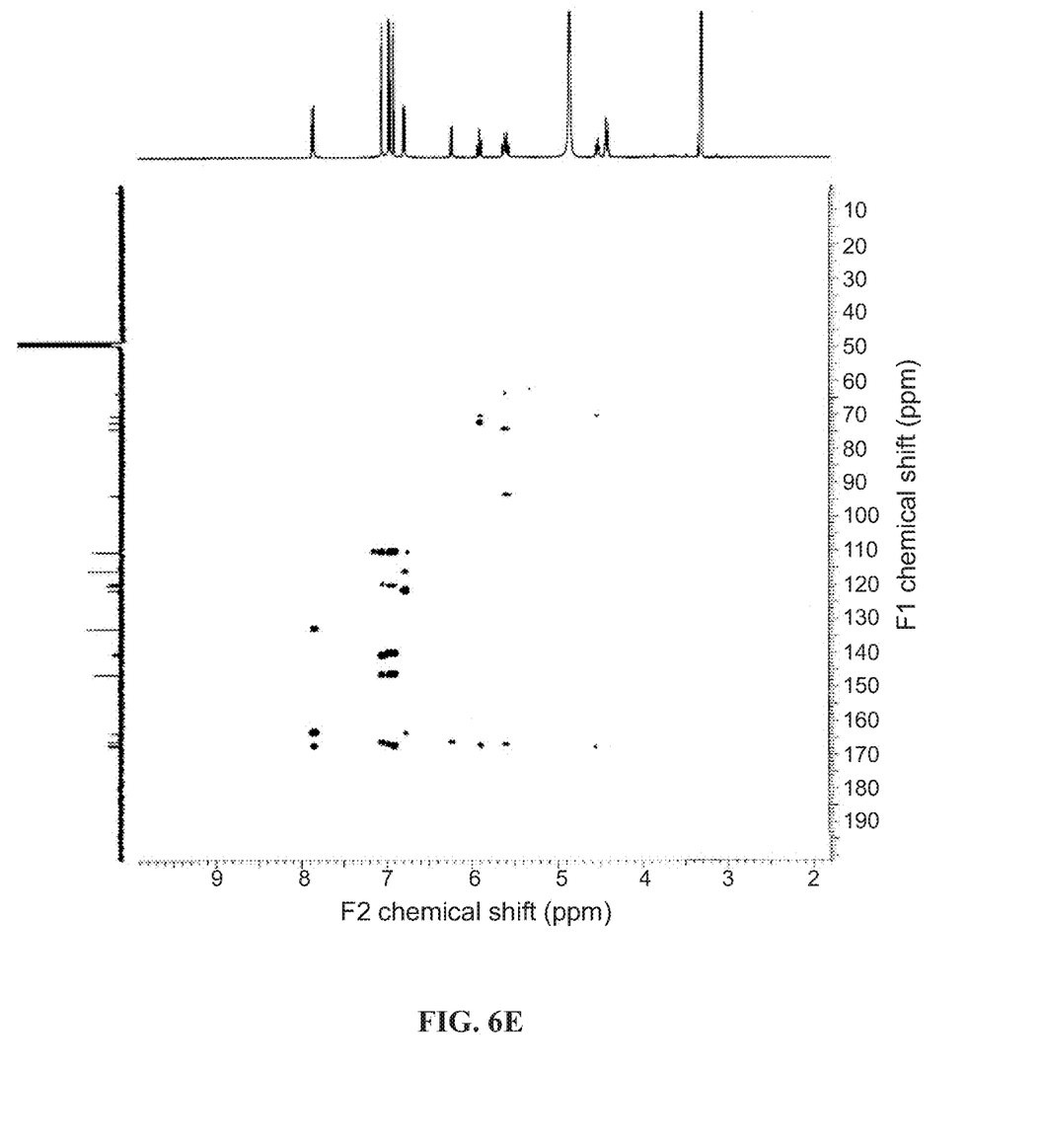
FIG. 6E shows the heteronuclear multiple bond correlation (HMBC) spectrum for compound 1.

Thus, compound 1 is identified as a hydrolyzable tannin that has not been reported and has the structure represented by formula (I). Compound 2 is identified, based on the mass and NMR spectra, as a hydrolyzable tannin having the structure represented by formula (II).

(I)

(II)

Example 6

Glycation-Suppressing Activity of the Compound of Formula (I) and Formula (II)

In order to evaluate the anti-glycation activity of the compounds of formula (I) and formula (II), the anti-glycation assay as described in Example 4 were performed to determine the inhibitory effect of the compounds on glycation of porcine collagen. Briefly, a mixture of 0.2 mL of the collagen solution and 0.2 mL of the fructose solution was mixed thoroughly with 0.2 mL of 100 µg/mL aqueous solution of the compound of formula (I) or formula (II), or mixed with deionized water (as a control). The reaction mixtures were incubated at 50° C. for 24 hours, and the fluorescence intensity of each of the mixtures (0.1 mL) at 0 hours and 24 hours was measured to calculate the rate of AGEs formation due to collagen glycation.

Figure 7:
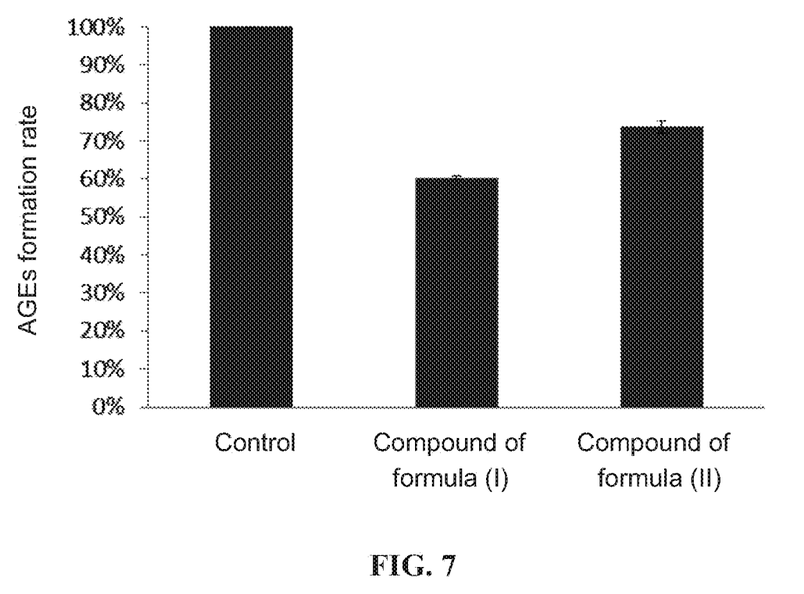
FIG. 7 shows the effect of the compounds of formula (I) and formula (II) on AGEs formation due to collagen glycation.

FIG. 7 shows the effect of the compounds of formula (I) and formula (II) on AGEs formation due to collagen glycation. According to this figure, treatment with the compounds of formula (I) and formula (II) significantly reduced AGEs formation to about 60.2% and 73.7%, respectively, compared to the control, indicating that the two compounds have significant anti-glycation activity.

In conclusion, the present invention discloses that the green mango extract has ultraviolet protection and skin-whitening effects on skin cells, and also inhibits protein glycation and avoids loss of normal structure and function of proteins due to glycation. Furthermore, the present invention also discloses the compounds of formula (I) and formula (II) that possess significant anti-glycation activities. Given that ultraviolet radiation, excessive melanin accumulation, and glycation all lead to the appearance of skin aging, especially glycation is one of the causes of body aging, and given that the green mango extract and compounds disclosed herein can be utilized in preparation of a composition for skin whitening, ultraviolet radiation protection, and anti-glycation, the present invention provides a new strategy to delay the aging of skin and even the aging of individuals. The composition may be in the form of powders, granules, solution, gel or paste and may be manufactured as a pharmaceutical composition, food, a drink, or a nutritional supplement that may be administered to a subject orally, topically or via other routes.

The present invention has been described with reference to the above preferred embodiments. However, it will be apparent to those skilled in the art that modifications and changes in form and detail may be made without departing from the scope of the present invention defined by the appended claims.

What is claimed is:

1. A method for whitening the skin of a human in need thereof comprising administering to the skin of the human in need thereof a skin whitening effective amount of an aqueous extract of a green mango fruit to the human in need thereof to effectively whiten the skin of the human in need thereof.

2. The method of claim 1, wherein the weight ratio of an aqueous solution for extracting the green mango fruit to the green mango fruit ranges from 20:1 to 1:1.

3. The method of claim 1, wherein the process for obtaining the aqueous extract of the green mango fruit is performed at a temperature between 55° C. and 100° C.

4. The method of claim 1, wherein the skin whitening effective amount is at least 0.25 mg/mL.

5. The method of claim 1, wherein the aqueous extract of the green mango fruit suppresses glycation of collagen in the human in need thereof.

* * * * *